United States Patent
Hogan et al.

(10) Patent No.: US 8,957,240 B2
(45) Date of Patent: *Feb. 17, 2015

(54) METHOD FOR THE PURIFICATION OF PROSTAGLANDINS

(71) Applicant: Johnson Matthey Public Limited Company, London (GB)

(72) Inventors: Robert R. Hogan, West Grove, PA (US); Ronald Rossi, Mullica Hill, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,236

(22) Filed: Jul. 29, 2013

(65) Prior Publication Data

US 2013/0317249 A1    Nov. 28, 2013

Related U.S. Application Data

(63) Continuation of application No. 12/820,610, filed on Jun. 22, 2010, now Pat. No. 8,519,178.

(60) Provisional application No. 61/219,166, filed on Jun. 22, 2009.

(51) Int. Cl.
  *C07C 61/06* (2006.01)
  *C07C 69/76* (2006.01)
  (Continued)

(52) U.S. Cl.
  CPC ............. *C07C 69/732* (2013.01); *C07C 405/00* (2013.01); *C07D 307/93* (2013.01); *C07D 307/937* (2013.01); *C07C 323/56* (2013.01); *C07C 2101/08* (2013.01); *C07C 2103/14* (2013.01)
  USPC .............. 560/121; 560/61; 562/503; 564/171

(58) Field of Classification Search
  USPC ....................... 560/61, 121; 562/503; 564/171
  See application file for complete search history.

(56) References Cited

U.S. PATENT DOCUMENTS 7,498,458 B2    3/2009  Greenwood et al.
8,519,178 B2 *  8/2013  Hogan et al. .................. 560/121

FOREIGN PATENT DOCUMENTS

CA    2275557 A1    12/1999
JP    4-112866 A    4/1992
(Continued)

OTHER PUBLICATIONS

Brunner et al., "Scale Up on Supercritical Fluid Chromatography (SFC)," in *Supercritical Fluids*, ed. E. Kiran et al. (Kluwer Academic Publishers, 1994), pp. 653-668.

(Continued)

*Primary Examiner* — T. Victor Oh
(74) *Attorney, Agent, or Firm* — RatnerPrestia (57) ABSTRACT

The present invention provides a method for the purification of a prostaglandin by supercritical fluid chromatography, said method comprising the use of a stationary phase and a mobile phase comprising carbon dioxide, provided that when the stationary phase is unmodified silica gel, the prostaglandin is not luprostiol. The invention also provides prostaglandins obtainable by the method.

13 Claims, 3 Drawing Sheets

(51) Int. Cl.
*C07C 69/74* (2006.01)
*C07C 233/00* (2006.01)
*C07C 69/732* (2006.01)
*C07C 405/00* (2006.01)
*C07D 307/93* (2006.01)
*C07D 307/937* (2006.01)
*C07C 323/56* (2006.01)

(56) References Cited

FOREIGN PATENT DOCUMENTS

| | | |
|---|---|---|
| JP | 09-104894 A | 4/1997 |
| JP | 2000-53640 A | 2/2000 |
| JP | 2005-503354 A | 2/2005 |
| JP | 2008-543825 A | 12/2008 |
| WO | WO-01/55101 | 8/2001 |
| WO | WO 02/096898 A2 | 12/2002 |
| WO | WO-2005/061480 | 7/2005 |
| WO | WO 2006/134467 A1 | 12/2006 |
| WO | WO-2009/136281 | 11/2009 |

OTHER PUBLICATIONS

Koski et al, "Analysis of prostaglandins in aqueous solutions by supercritical fluid extraction and chromatography," *Journal of Pharmaceutical & Biomedical Analysis*, 1991, vol. 9., No. 4, pp. 281-290.

David et al., "Analysis of Derivatised Prostaglandins by Capillary Supercritical Fluid Chromatography with a Phosphorus-Selective Detector," *J. Microcolumn Separations*, 1998, vol. 10, No. 1, pp. 27-32.

Markides et al., "Capillary Superficial Fluid Chromatography of Labile Carboxylic Acids," *Journal of Chromatographic Science*, Preston Publications, Niles, IL, US, vol. 24, Jun. 1, 1986, pp. 254-257.

Levin, S. et al., "Resolution of Chiral Cannabinoids n Amylose Tris(3,5-dimethylphenylcarbamate) Chiral Stationary Phase: Effects of Structural Features and Mobile Phase Additives," *Journal of Chromatography*, Elsevier Science Publishers, vol. 654, Jan. 1, 1993, pp. 53-64.

Translation of Notification of Reasons For Rejection, Japanese Patent Application No. JP 2012-517644, Mailed Feb. 25, 2014, 7 pp.

* cited by examiner

FIG. 1

LATANOPROST ISOMERS

C15S-cis

CHEMICAL FORMULA: $C_{26}H_{40}O_5$
MOLECULAR WEIGHT: 432.59

C11-beta

CHEMICAL FORMULA: $C_{26}H_{40}O_5$
MOLECULAR WEIGHT: 432.59

C15R-trans

CHEMICAL FORMULA: $C_{26}H_{40}O_5$
MOLECULAR WEIGHT: 432.59

C15S-trans

CHEMICAL FORMULA: $C_{26}H_{40}O_5$
MOLECULAR WEIGHT: 432.59

METHOD FOR THE PURIFICATION OF PROSTAGLANDINS

CROSS-REFERENCE TO RELATED APPLICATION

This application is a continuation of U.S. patent application Ser. No. 12/820,610, filed Jun. 22, 2010, and claims priority to U.S. Provisional Application No. 61/219,166, filed Jun. 22, 2009, the disclosures of both of which are incorporated herein by reference in their entireties for all purposes.

FIELD OF THE INVENTION

The present invention provides a method for the purification of prostaglandins. In particular, the present invention provides a method for the purification of prostaglandins by supercritical fluid chromatography (SFC).

BACKGROUND OF THE RELATED ART

Prostaglandins are active pharmaceutical ingredients (APIs) and isomerically and chemically pure prostaglandins are required for formulation into drug products. However, the purification of prostaglandins is challenging due to the similar chemical properties of many prostaglandin isomers, as well as their related impurities.

G. H. Brunner et al. (Supercritical Fluids, 653-668, E. Kiran and J. M. H. Levelt Sengers (eds.), Kluwer Academic Publishers, 1994) describes the preparative supercritical fluid chromatography (SFC) separation of Reprodin isomers (i.e. luprostiol isomers). However, the isomers are poorly separated and the purity of the heart cut fraction is only 80%. This method therefore cannot be used to obtain a commercial product as the purity does not meet ICH quality. The authors acknowledge that SFC is disadvantageous in comparison to liquid chromatography.

BRIEF SUMMARY OF THE INVENTION

The present inventors, however, have overcome the problems associated with the prior art procedure to provide an alternative process for the purification of prostaglandins using SFC.

Accordingly, the present invention provides a method for the purification of a prostaglandin by supercritical fluid chromatography, said method comprising the use of a stationary phase and a mobile phase comprising carbon dioxide, provided that when the stationary phase is unmodified silica gel, the prostaglandin is not luprostiol. For example, the invention includes a method for purifying a crude prostaglandin, comprising injecting the crude prostaglandin onto a column comprising a stationary phase, eluting the crude prostaglandin through the column using a mobile phase comprising supercritical carbon dioxide, and collecting a fraction comprising a purified prostaglandin.

DETAILED DESCRIPTION OF THE INVENTION

By "purification", it is meant the method produces a prostaglandin which is chemically and/or isomerically pure. A chemically pure compound is one where the compound is essentially free from related compounds, chemical starting materials, chemical intermediates and chemical degradants. An isomerically pure compound is one where the compound is essentially free from known related compounds of the same chemical molecular formula that are different in chemical structure.

In one embodiment, the purified prostaglandin is at least about 99% chemically pure, preferably at least about 99.5% chemically pure and more preferably at least about 99.8% chemically pure.

In another embodiment, the purified prostaglandin is at least 99% isomerically pure, preferably at least about 99.5% isomerically pure and more preferably at least about 99.9% isomerically pure.

The method of the present invention may be utilised to purify a prostaglandin on an analytical or preparative scale. By "analytical", we mean a scale of providing at least about 0.1 mg of purified prostaglandin, preferably about 1 mg of purified prostaglandin, in a reasonable timeframe, i.e. less than a day. By "preparative", we mean a scale of providing at least about 1 mg of purified prostaglandin, preferably about 0.1 g of purified prostaglandin and most preferably about 1 g of purified prostaglandin, in a reasonable timeframe, i.e. less than a day.

Preferably, the prostaglandin is a compound of formula (I), a compound of formula (II), a compound of formula (III) or a compound of formula (IV):

(IV)

wherein,
V is C or O;
W is

X is $CONR_{12}R_{13}$ or $CO_2R_{12}$;
Y is

Z is $C_{1-20}$-alkyl, $C_{2-20}$-alkynyl, —O—($C_{6-20}$-aryl) or —($C_{1-20}$-alkyl)-($C_{6-20}$-aryl), wherein the aryl group is optionally substituted with one to three substituents selected from the group consisting of $C_{1-20}$-alkyl, halo and $C(halo)_3$;

$R_1$ and $R_2$ are independently H or OH, or $R_1$ and $R_2$ together form $R_3$ and $R_4$ are independently H or OH;
$R_5$ and $R_6$ are independently H or OH, or $R_5$ and $R_6$ together form $R_7$ and $R_8$ are independently H, OH, halo or $C_{1-20}$-alkyl;
$R_9$ and $R_{10}$ are independently H or $C_{1-20}$-alkyl, wherein the alkyl group is optionally substituted with one or more substituents selected from $CONR_{12}R_{13}$, $CO_2R_{12}$ or $CO_2^-M^+$;
$R_{11}$ is $C_{1-20}$-alkyl or —O—($C_{1-20}$-alkyl), wherein the alkyl group is optionally substituted with one or more substituents selected from $CONR_{12}R_{13}$, $CO_2R_{12}$ or $CO_2^-M^+$;

$R_{12}$ and $R_{13}$ are independently selected from the group consisting of H and $C_{1-20}$ alkyl;

$M^+$ is a counter cation; and

Halo is fluorine, chlorine, bromine or iodine. When V=C, it is understood that the carbon atom bears two hydrogen atoms, one or both of which may be substituted with a substituent group which may be independently selected from halo and $C_{1-20}$-alkyl, for example.

"Alkyl" refers to linear, branched or cyclic saturated hydrocarbon structures having, unless otherwise indicated, 1 to 20 carbon atoms, more preferably 1 to 15 carbon atoms and most preferably 1 to 10 carbon atoms. Examples of alkyl groups are methyl, ethyl, n-propyl, isopropyl, cyclopropyl, n-butyl, i-butyl, t-butyl, n-pentyl, n-hexyl and cyclohexyl. When an alkyl group having a specific number of carbons atoms is named, it is intended that all geometric isomers of that alkyl group are encompassed. For example, "butyl" includes n-butyl, i-butyl, t-butyl and cyclobutyl.

"Alkynyl" refers to linear or branched hydrocarbon structures having at least one group and, unless otherwise indicated, 2 to 20 carbon atoms, more preferably 2 to 15 carbon atoms and most preferably 2 to 10 carbon atoms. Examples of alkynyl groups are ethynyl, propynyl, n-butynyl, isobutynyl and hexynyl. When an alkynyl group having a specific number of carbon atoms is named, it is intended that all geometric isomers of that alkynyl group are encompassed. For example "butynyl" includes n-butynyl and isobutynyl.

"Aryl" refers to an aromatic hydrocarbon structure having, unless otherwise indicated, 6 to 20 carbon atoms, more preferably 6 to 15 carbon atoms and most preferably 6 to 10 carbon atoms. Examples of aryl groups are phenyl and naphthyl.

The term "halo" whether alone or as part of another group refers to a halogen, for example, a fluorine, chlorine, bromine or iodine atom.

$M^+$ is a counter cation of —$CO_2^-$ i.e. —$CO_2^-M^+$ is a carboxylic acid salt and preferably a pharmaceutically acceptable carboxylic acid salt. Preferably $M^+$ is a metal ion e.g. an alkali metal ion, such as $K^+$ or $Na^+$.

Preferably, W is

X is preferably $CONH(C_{1-10}$-alkyl), $CO_2(C_{1-10}$-alkyl) or $CO_2H$. More preferably, X is selected from the group consisting of CONHEt, $CO_2Me$, $CO_2^iPr$ and $CO_2H$.

Preferably, Z is $C_{1-10}$-alkyl, $C_{2-10}$-alkynyl, —O—($C_{6-10}$-aryl) or —($C_{1-10}$-alkyl)-($C_{6-10}$-aryl), wherein the aryl group is optionally substituted with one to three substituents selected from the group consisting of Cl and —$CF_3$. More preferably, Z is —$(CH_2)_5CH_3$, —$(CH_2)_3CH_3$, —$CH_2$-Ph, $R_1$ and $R_2$ may independently be H or OH. Preferably, when one of $R_1$ and $R_2$ is H, the other of $R_1$ and $R_2$ is OH.

When $R_5$ and $R_6$ together form and one of $R_3$ and $R_4$ is OH and the other of $R_3$ and $R_4$ is H, it is possible for a tautomer to be produced i.e. a hemiacetal. It is envisaged that such tautomers are encompassed with the scope of the present invention. A tautomeric equilibrium is exemplified by the prostaglandin lubiprostone:

More preferably, when one of $R_1$ and $R_2$ is H and the other of $R_1$ and $R_2$ is OH, $R_1$, $R_2$ and the carbon atom to which they are attached have the following stereochemistry:

$R_3$ and $R_4$ are independently H or OH. Preferably, when one of $R_3$ and $R_4$ is H, the other of $R_3$ and $R_4$ is OH. More preferably, $R_3$, $R_4$ and the carbon atom to which they are attached have the following stereochemistry:

$R_5$ and $R_6$ may independently be H or OH. In one embodiment, when one of $R_5$ and $R_6$ is H, the other of $R_5$ and $R_6$ is OH. More preferably, when one of $R_5$ and $R_6$ is H and the other of $R_5$ and $R_6$ is OH, $R_5$, $R_6$ and the carbon atom to which they are attached have the following stereochemistry:

In another embodiment, $R_5$ and $R_6$ are both H.

Preferably, $R_7$ and $R_8$ are independently selected from the group consisting of H, OH, F or $CH_3$. In one embodiment, $R_7$ and $R_8$ are both H. In another embodiment, $R_7$ and $R_8$ are both F. In yet another embodiment, one of $R_7$ and $R_8$ is $CH_3$ and the other of $R_7$ and $R_8$ is H or OH.

Preferably, $R_9$ and $R_{10}$ are independently H or $C_{1-10}$-alkyl, wherein the alkyl group is optionally substituted with one or more substituents selected from $CO_2H$ or $CO_2^-M^+$. More preferably, one of $R_9$ and $R_{10}$ is H and the other of $R_9$ and $R_{10}$ is —$(CH_2)_3CO_2H$ or —$(CH_2)_3CO_2^-Na^+$.

Preferably, $R_{11}$ is $C_{1-10}$-alkyl or —O—($C_{1-10}$-alkyl), wherein the alkyl group is optionally substituted with one or more substituents selected from $CO_2H$ or $CO_2^-M^+$. More preferably, $R_{11}$ is —$(CH_2)_3CO_2H$ or —O—$CH_2$—$CO_2H$.

In a preferred embodiment, the prostaglandin is selected from the group consisting of:

Latanoprost

Bimatoprost

Travoprost

Cloprostenol

Fluprostenol

Unoprotone

Dinoprostone

Dinoprost

Lubiprostone

Misoprotol

Alprostadil

Beraprost

Ilaprost

Epoprostenol Sodium

Treprostenil

Preferably, the prostaglandin is latanoprost.

Alternatively, if the stationary phase is other than unmodified silica gel, the prostaglandin can be luprostiol:

Luprostiol

In one embodiment, the stationary phase is a chiral stationary phase. Preferably, the chiral stationary phase is a derivatised amylose or cellulose polymer or other polysaccharide which is coated or immobilized on silica. More preferably, the chiral stationary phase is selected from the group consisting of Chiralcel OD-H, ChiralPak AS-H, ChiralPak IC, ChiralPak AD-H, Chiralcel OJ-H and Chiralcel OK (products available from Chiral Technologies Inc. and Daicel Chemical Industries, Ltd.). More preferably, the chiral stationary phase is ChiralPak AD-H. For example, the amylase or cellulose polymer may be derivatised with one or more carbamate groups, especially aryl-containing carbamate groups such as 3,5-dimethylphenylcarbamate, (S)-alpha-methylbenzylcarbamate, 4-chlorophenyl carbamate, 4-methylphenylcarbamate, phenyl carbamate, 3-chloro-4-methyl phenylcarbamate, 5-chloro-2-methyl phenylcarbamate or the like, and/or one or more ester groups, such as acetate, benzoate (e.g., 4-methyl benzoate), cinnamate, or the like.

In another embodiment, the stationary phase is a non-chiral stationary phase. Preferably, the non-chiral stationary phase is selected from the group consisting of Princeton Diol, 4-ethyl pyridine, 2-ethyl pyridine and pyridine urea.

Preferably, the mobile phase further comprises at least one modifier. The modifier can be any suitable liquid solvent. A suitable modifier may be selected from the group consisting of at least one alcohol, acetonitrile, ethyl acetate, methylene chloride and a combination thereof. Preferably, the at least one alcohol is selected from the group consisting of methanol, ethanol, propanol, isopropanol and a combination thereof. It is desirable that the modifier is compatible with the stationary phase. For example, ethyl acetate and methylene chloride cannot be used with a ChiralPak AD column as they will destroy the column.

Carbon dioxide is easily removed and so, the purified prostaglandin can be provided as a solution with the modifier as a solvent. It may therefore be desirable to select a modifier in which the prostaglandin is soluble.

Suitably, the at least one modifier is present in a quantity from (i.e., of at least) about 1% v/v or about 1% w/w to the supercritical carbon dioxide. More preferably, the at least one modifier is present in a quantity from (i.e., of at least) about 5% v/v or about 5% w/w to the supercritical carbon dioxide. The ratio of modifier to carbon dioxide can be varied during the chromatographic process.

Suitable chromatographic apparatus is well known to the skilled person. It is preferred to use an apparatus that is suitable for Supercritical Fluid Chromatography such as the Thar Investigator SFC or Novasep Supersep 20/30 SFC. The crude feed containing the crude prostaglandin is periodically injected into the apparatus wherein the mobile phase flows through the stationary phase which is located in a column. After detection at the column outlet, the purified fractions of the feed are directed to different traps. The carbon dioxide is removed from the purified fractions and is preferably recycled. Detection at the column outlet can be conducted by measuring UV absorption at an appropriate wavelength.

On an analytical scale, the column diameter is suitably from about 2 mm to about 7 mm, preferably about 4.6 mm. The column length is suitably from about 5 cm to about 50 cm, preferably about 25 cm.

On a preparative scale, the column diameter is suitably from about 10 mm to about 200 mm, preferably about 21 mm. The column length is suitably from about 5 cm to about 50 cm, preferably about 25 cm.

The process is suitably carried out at temperatures from about 5° C. to about 45° C., preferably about 25° C. to about 35° C., and at elevated pressures e.g. from about 80 bar to 300 bar, preferably about 100 bar to 150 bar. Typical flow rates depend upon the diameter of the column and may vary from e.g. 1 mL/min to about 5 kg/min.

In another aspect, the present invention provides a prostaglandin obtainable by a method as described above.

The following Examples are illustrative but not limiting of the invention.

Example 1

Analytical Scale

SFC Preparatory Parameters:
Column: Chiral Technologies Chiralpak AD-H, 4.6×250 mm
Column Temperature: 35° C.
System Back Pressure: 150 Bar
Eluent: Carbon Dioxide ($CO_2$) with an alcoholic modifier, Ethanol
Total Flow Rate: 3 mL/min
Gradient Co-Solvent Profile: Initial conditions=5% Ethanol: 95% $CO_2$, linearly increase to 45% Ethanol: 55% $CO_2$ in 15 minutes, maintain 45% Ethanol: 55% $CO_2$ for 2 minutes, ramp back to initial conditions and equilibrate for 3 minutes prior to next injection
Detection: UV at 210 nm
Sample Preparation: Prepare a 0.1 g/mL solution in Ethanol and thoroughly mix the feed solution to completely dissolve the Latanoprost
Sample Loading: 5 mg (50 µL of 0.1 g/mL crude solution in Ethanol)
Latanoprost Collection: Collect the Latanoprost peak (heart cut) from approximately 2% above the baseline from the detected Latanoprost peak front (at ~9 minutes in retention time) to the Latanoprost detected peak tail (at ~10 minutes in retention time).

Figure 1:
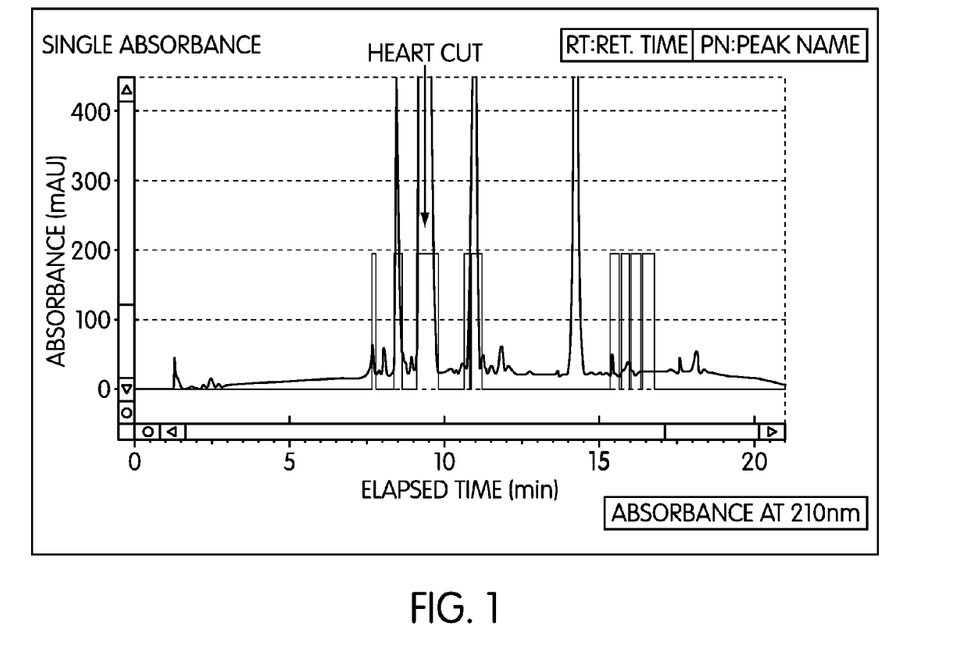
FIG. 1 illustrates a chromatogram of a SFC purification injection of crude latanoprost, obtained as described in Example 1.

The chromatogram of a SFC purification injection of Latanoprost Crude is provided in FIG. 1.

Obtained Results using Ethanol as the Co-Solvent and AD-H Stationary Phase:

| | Chromatographic Purity-Reported as Measured % Peak Area | | | | | |
|---|---|---|---|---|---|---|
| | | | Isomeric Content* | | | |
| | Latanoprost | | C11- | C15R- | C15S- | C15S- |
| Sample | Chemical | Isomeric | beta | trans | cis | trans |
| Crude Feed (0.01 g/mL) | 95.87% | 90.02% | 1.11% | 3.88% | 3.04% | 0.05% |
| Heart Cut (5 mg Loading) | 99.95% | 99.92% | — | — | 0.08% | — |

Figure 2:
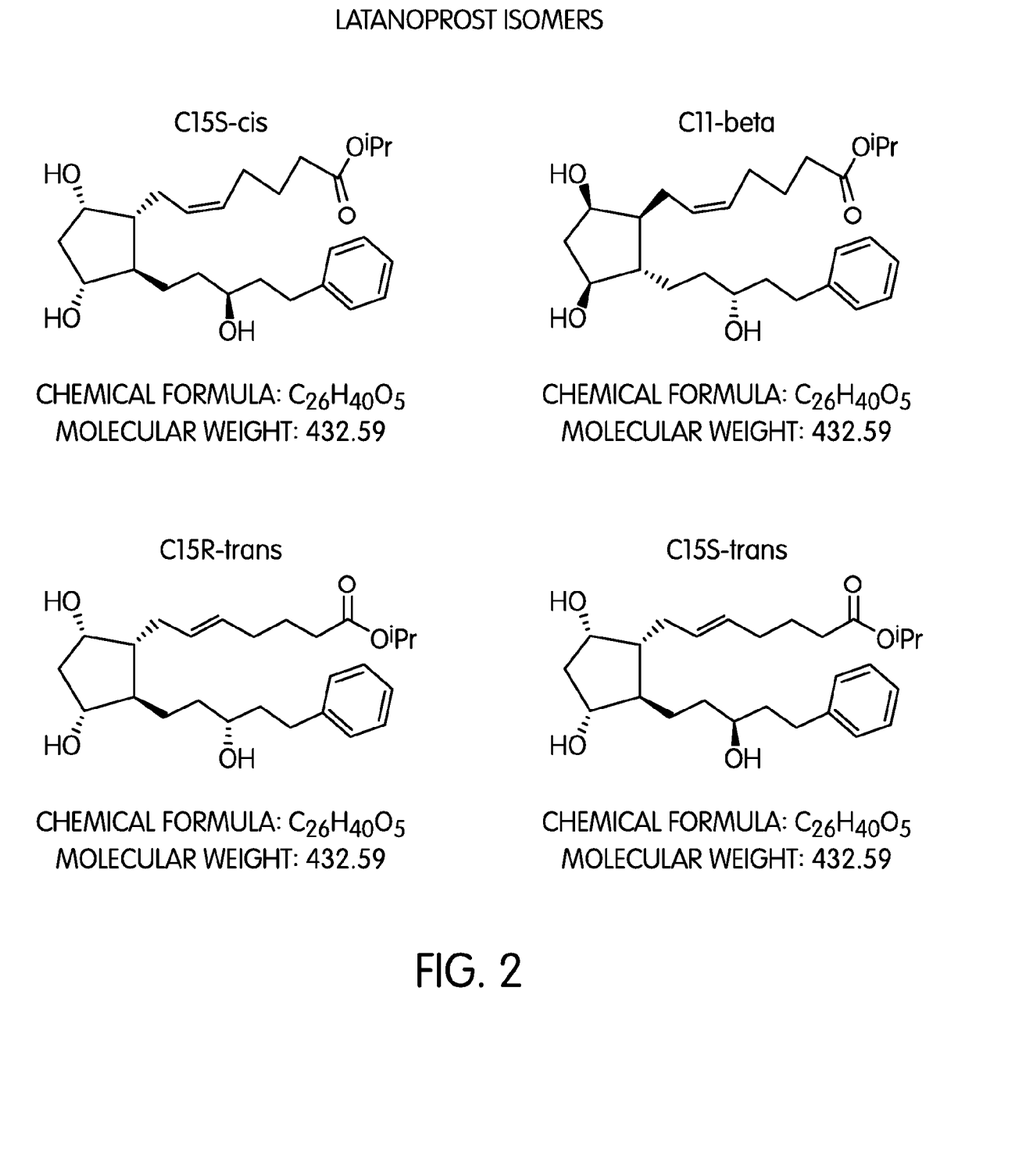
FIG. 2 sets out the structures of latanoprost isomers.

*The structures of the latanoprost isomers are set out in FIG. 2.

Example 2

Preparative Scale

SFC Preparatory Parameters:

Column: Chiral Technologies Chiralpak AD-H, 21×250 mm

Column Temperature: 25° C.

System Back Pressure: 100 Bar

Eluent: Carbon Dioxide ($CO_2$) with an alcoholic Co-solvent modifier (specifically Ethanol: Methanol (4:1))

Total Flow Rate: 50 g/min

Co-Solvent Profile: Initial conditions=15% Co-solvent: 85% $CO_2$, for 360 seconds, Step to 40% Co-solvent: 60% $CO_2$ at 361 seconds until 720 seconds, step back to initial conditions at 721 seconds until 900 seconds Detection: UV at 220 nm Crude Solution Preparation: Prepare a 0.3 g/mL solution in Ethanol and thoroughly mix the feed solution to completely dissolve the Latanoprost Sample Loading: ~0.6 mL crude solution in Ethanol Latanoprost Collection: Collect the Latanoprost peak (heart cut) from approximately 30 seconds after peak start the baseline from the detected Latanoprost peak front (at ~410 seconds in retention time) to approximately 30 seconds prior to the peak end (at ~510 seconds in retention time).

Figure 3:
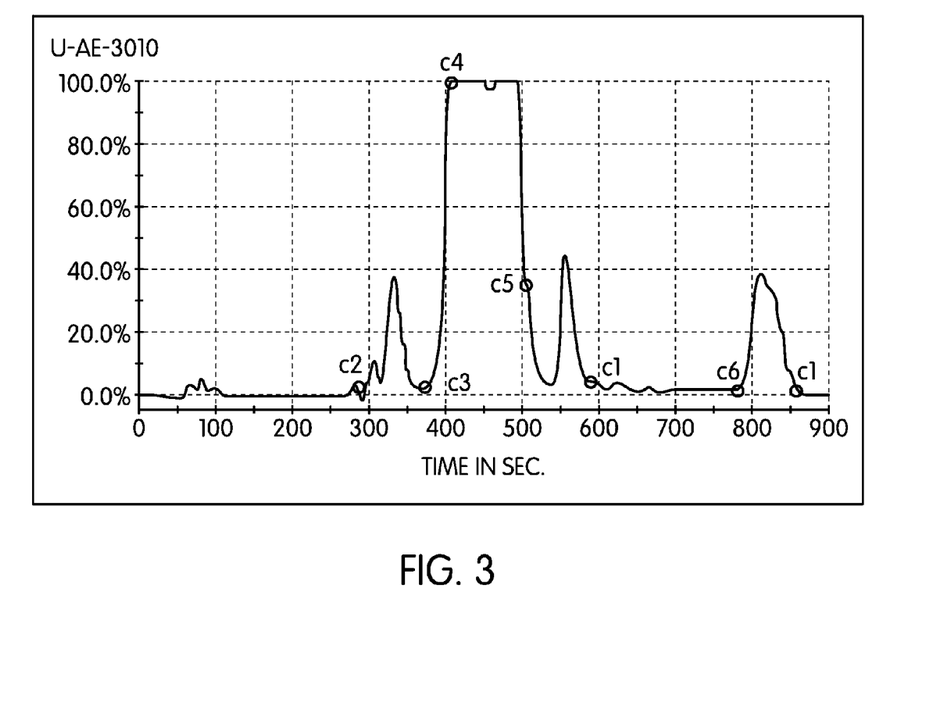
FIG. 3 illustrates a chromatogram of a SFC purification injection of crude latanoprost, obtained as described in Example 2.

The chromatogram of a SFC purification injection of Latanoprost Crude is provided in FIG. 3.

Obtained Results using Ethanol as the Co-Solvent and AD-H Stationary Phase of the collected fractions:

| | Chromatographic Purity-Reported as Measured % Peak Area | | | | | |
|---|---|---|---|---|---|---|
| | | | Isomeric Content§ | | | |
| | Latanoprost | | C11- | C15R- | C15S- | C15S- |
| Sample | Chemical | Isomeric | beta | trans | cis | trans |
| Crude Feed | 96.51% | 93.07% | 0.70% | 2.79% | 2.15% | 0.06% |
| Purified Heart Cut | 99.81%* | 99.98% | — | — | 0.02% | — |

*No impurities measured above 0.04% by percent peak area.
§The structures of the latanoprost isomers are set out in FIG. 2.

No isomers were detected after 11 months storage at freezer temperature when the purified Latanoprost was analyzed with a typical HPLC method for isomer content determination to the following detection levels:

| Isomer | Detection Limit |
|---|---|
| C11-beta | 0.03% |
| C15R-Trans | 0.03% |
| C15S-Trans | 0.05% |
| C15S-Cis | 0.03% |
| Latanoprost | 0.03% |

What is claimed:

1. A method for the purification of a prostaglandin by supercritical fluid chromatography, said method comprising using a stationary phase and a mobile phase comprising carbon dioxide, wherein the stationary phase is diol and the prostaglandin is a compound of formula (I), a compound of formula (II), or a compound of formula (IV):

(I)

(II)

-continued

(IV)

wherein,
V is C;
W is

;

X is $CONR_{12}R_{13}$ or $CO_2R_{12}$;
Y is

;

Z is $C_{1-20}$-alkyl, $C_{2-20}$-alkynyl, —O—($C_{6-20}$-aryl) or —($C_{1-20}$-alkyl)-($C_{6-20}$-aryl), wherein the aryl group is optionally substituted with one to three substituents selected from the group consisting of $C_{1-20}$-alkyl, halo and C(halo)$_3$;
$R_1$ and $R_2$ are independently H or OH, or $R_1$ and $R_2$ together form

$R_3$ and $R_4$ are independently H or OH;
$R_5$ and $R_6$ are independently H or OH, or $R_5$ and $R_6$ together form

$R_7$ and $R_8$ are independently H, OH, halo or $C_{1-20}$-alkyl; $R_9$ and $R_{10}$ are independently H or $C_{1-20}$-alkyl, wherein the alkyl group is optionally substituted with one or more substituents selected from $CONR_{12}R_{13}$, $CO_2R_{12}$, and $CO_2^-M^+$; $R_{11}$ is $C_{1-20}$-alkyl or —O—($C_{1-20}$-alkyl), wherein the alkyl group is optionally substituted with one or more substituents selected from $CONR_{12}R_{13}$, $CO_2R_{12}$, and $CO_2^-M^+$; $R_{12}$ and $R_{13}$ are independently selected from the group consisting of H and $C_{1-20}$ alkyl; $M^+$ is a counter cation; and Halo is fluorine, chlorine, bromine or iodine.

2. A method according to claim 1, wherein the prostaglandin is selected from the group consisting of:

Latanoprost

Bimatoprost

Travoprost

Cloprostenol

Fluprostenol

Unoprotone

Dinoprostone

Dinoprost

Lubiprostone

Misoprotol

Alprostadil

Treprostenil

3. A method according to claim 1, wherein the prostaglandin is:

Luprostiol

4. A method according to claim 1, wherein the mobile phase further comprises at least one modifier.

5. A method according to claim 4, wherein the at least one modifier is selected from the group consisting of at least one alcohol, acetonitrile, ethyl acetate, methylene chloride and a combination thereof.

6. A method according to claim 4, wherein the at least one modifier includes an alcohol selected from the group consisting of methanol, ethanol, propanol, isopropanol and a combination thereof.

7. A method according to claim 4, wherein the at least one modifier is present in a quantity from about 1% v/v to the carbon dioxide.

8. A method according to claim 4, wherein the at least one modifier is present in a quantity from about 1% w/w to the carbon dioxide.

9. A method according to claim 4, wherein the at least one modifier is present in a quantity from about 5% v/v to the carbon dioxide.

10. A method according to claim 4, wherein the at least one modifier is present in a quantity from about 5% w/w to the carbon dioxide.

11. A method according to claim 1, wherein the method provides a purified prostaglandin which is at least 99% chemically pure.

12. A method according to claim 1, wherein the method provides a purified prostaglandin which is at least 99% isomerically pure.

13. A method for purifying a crude prostaglandin, comprising injecting the crude prostaglandin onto a column comprising a stationary phase, eluting the crude prostaglandin through the column using a mobile phase comprising supercritical carbon dioxide, and collecting a fraction comprising a purified prostaglandin, wherein the stationary phase is diol and the prostaglandin is a compound of formula (I), a compound of formula (II), or a compound of formula (IV):

(I)

(II)

(IV)

wherein,
V is C;
W is

;

X is CONR$_{12}$R$_{13}$ or CO$_2$R$_{12}$;
Y is or ;

Z is C$_{1-20}$-alkyl, C$_{2-20}$-alkynyl, —O—(C$_{6-20}$-aryl) or —(C$_{1-20}$-alkyl)-(C$_{6-20}$-aryl), wherein the aryl group is optionally substituted with one to three substituents selected from the group consisting of C$_{1-20}$-alkyl, halo and C(halo)$_3$;

R$_1$ and R$_2$ are independently H or OH, or R$_1$ and R$_2$ together form

;

R$_3$ and R$_4$ are independently H or OH;

R$_5$ and R$_6$ are independently H or OH, or R$_5$ and R$_6$ together form

;

R$_7$ and R$_8$ are independently H, OH, halo or C$_{1-20}$-alkyl;

R$_9$ and R$_{10}$ are independently H or C$_{1-20}$-alkyl, wherein the alkyl group is optionally substituted with one or more substituents selected from CONR$_{12}$R$_{13}$, CO$_2$R$_{12}$, and CO$_2^-$M$^+$;

R$_{11}$ is C$_{1-20}$-alkyl or —O—(C$_{1-20}$-alkyl), wherein the alkyl group is optionally substituted with one or more substituents selected from CONR$_{12}$R$_{13}$, CO$_2$R$_{12}$, and CO$_2^-$M$^+$;

R$_{12}$ and R$_{13}$ are independently selected from the group consisting of H and C$_{1-20}$ alkyl;

M$^+$ is a counter cation; and

Halo is fluorine, chlorine, bromine or iodine.

* * * * *